United States Patent
Jordan et al.

(10) Patent No.: US 10,078,008 B2
(45) Date of Patent: Sep. 18, 2018

(54) LIGHT ASSEMBLY WITH INTEGRATED TEST FACILITY

(71) Applicant: OXLEY DEVELOPMENTS COMPANY LTD., Ulverston (GB)

(72) Inventors: Mark Jordan, Hest Bank (GB); Tom Ward, Ulverston (GB); Daniel Foster, Ulverston (GB); Timothy Lysons, Ulverston (GB); Andrzej Pelczar, Ulverston (GB); Mark Reynolds, Barrow-In-Furness (GB)

(73) Assignee: Oxley Developments Company Ltd., Ulverston (GB)

( * ) Notice: Subject to any disclaimer, the term of this patent is extended or adjusted under 35 U.S.C. 154(b) by 0 days.

(21) Appl. No.: 15/129,359

(22) PCT Filed: Mar. 26, 2015

(86) PCT No.: PCT/GB2015/050912
§ 371 (c)(1),
(2) Date: Sep. 26, 2016

(87) PCT Pub. No.: WO2015/145159
PCT Pub. Date: Oct. 1, 2015

(65) Prior Publication Data
US 2017/0176247 A1    Jun. 22, 2017

(30) Foreign Application Priority Data
Mar. 27, 2014    (GB) .................................. 1405549.5

(51) Int. Cl.
*G01J 1/42*    (2006.01)
*G01N 21/94*    (2006.01)
(Continued)

(52) U.S. Cl.
CPC .......... *G01J 1/4204* (2013.01); *B60Q 1/0023* (2013.01); *G01J 1/0422* (2013.01);
(Continued)

(58) Field of Classification Search
CPC ....................... G01N 21/47; G01N 2021/4704
See application file for complete search history.

(56) References Cited

U.S. PATENT DOCUMENTS 4,874,242 A    10/1989    Bezard et al.
6,624,418 B1    9/2003    Braunwarth et al.
(Continued)

FOREIGN PATENT DOCUMENTS

CN    101694280 A    4/2010
DE    19539422 A1    4/1997
(Continued)

OTHER PUBLICATIONS

United Kingdom Search Report dated Aug. 18, 2014 for UK Application No. GB1405549.5 from United Kingdom Intellectual Property Office, pp. 1-2, South Wales, United Kingdom.
(Continued)

*Primary Examiner* — Shawn Decenzo
(74) *Attorney, Agent, or Firm* — Sherman IP LLP; Kenneth L. Sherman; Steven Laut

(57) ABSTRACT

A light assembly, comprising: a base; at least one electromagnetic radiation source mounted on the base; a cover located over the base, the cover being transparent to the electromagnetic radiation produced by the electromagnetic radiation source; and at least one photo detector, optically isolated from the at least one electromagnetic radiation source, the at least one photo detector being configured to receive electromagnetic radiation conveyed by the cover.

31 Claims, 4 Drawing Sheets

(51) Int. Cl.
    *B60Q 1/00*     (2006.01)
    *H05B 33/08*     (2006.01)
    *G01J 1/04*     (2006.01)

(52) U.S. Cl.
    CPC ......... *G01N 21/94* (2013.01); *H05B 33/0893* (2013.01); *G01J 2001/4247* (2013.01)

(56) References Cited

U.S. PATENT DOCUMENTS

| | | | | |
|---|---|---|---|---|
| 2006/0226336 A1* | 10/2006 | York | ................. | G01J 1/02 250/206 |
| 2011/0001431 A1* | 1/2011 | Brukilacchio | ............ | F21K 9/00 315/152 |
| 2011/0129213 A1* | 6/2011 | Painchaud | ........... | H04B 10/676 398/16 |
| 2014/0268790 A1* | 9/2014 | Chobot | ............... | F21V 23/0464 362/276 |

FOREIGN PATENT DOCUMENTS

| | | |
|---|---|---|
| DE | 10000291 A1 | 7/2001 |
| DE | 102004035438 A1 | 2/2006 |
| EP | 1039279 A2 | 9/2000 |
| WO | 2006099732 A1 | 9/2006 |
| WO | 2011002508 A2 | 1/2011 |

OTHER PUBLICATIONS

International Search Report and Written Opinion dated Sep. 1, 2015 for International Application No. PCT/GB2015/050912 from European Patent Office, pp. 1-17, Risjswijk Netherlands.

\* cited by examiner

LIGHT ASSEMBLY WITH INTEGRATED TEST FACILITY

BACKGROUND

This invention relates to a light assembly having an integrated test facility. In particular, this invention relates to a photo detector integrated with the light assembly that can be used to measure the quantity of the light flux distributed through a light output aperture of the light assembly.

Information about the quantity of the light flux distributed through the light output aperture of the light assembly is a critical safety parameter in many applications including, but not limited to, automotive signalling and position light assemblies and/or airborne signalling and position light assemblies and/or marine signalling and position light assemblies and/or submarine signalling and position light assemblies. The quantity of the light flux required for the specific application distributed through the light output aperture of the light assembly can be compromised during operational conditions, for a number of reasons.

The light flux distributed through the light output aperture can fluctuate as a result of changes in light source properties and/or a result of changes in optical properties of the light output aperture itself. Visual checking of the light assembly optical properties such as light beam geometry and/or intensity can be difficult to obtain and is often inaccurate. An unexpected accumulation of dust, ice or water vapour on the light output aperture and/or mechanical damage to the light output aperture can also decrease the lamp light flux without the lamp operators' awareness, and can lead to a catastrophic failure of the device containing such a light assembly.

In order to address these problems, various pieces of remote test equipment which use photo detectors have been developed to check and record the intensity, direction and angular distribution of the light assembly similar to that known in the automotive industry.

SUMMARY

It is an object of the present invention to provide a light assembly that includes an integrated test facility which can be used to provide monitoring of the light flux passing the light output aperture to indicate when the light output aperture is damaged or dirty, and/or the light source starts to degrade and may need replacement or repair. It is a further object of the present invention to provide a measurement of the light flux distributed through the light output aperture emitted from sources of light within the assembly in the presence of dynamically changing ambient light.

According to the present invention there is provided a light assembly, comprising:
  a base;
  at least one electromagnetic radiation source mounted on the base;
  a cover located over the base, the cover being transparent to the electromagnetic radiation produced by the electromagnetic radiation source; and
  at least one photo detector, optically isolated from the at least one electromagnetic radiation source, the at least one photo detector being configured to receive electromagnetic radiation conveyed by the cover.

By optically isolating the at least one photo detector from the at least one electromagnetic radiation source, the at least one photo detector is advantageously configured to receive electromagnetic radiation conveyed by the cover. An advantage of using the present invention for detecting the electromagnetic radiation emitted from the at least one electromagnetic radiation source is that an operator is quickly able to diagnose that the electromagnetic radiation source is failing, or is about to fail, or that the cover surrounding the electromagnetic radiation source is dirty or damaged. It is to be understood that term "optically isolated" is intended to define arrangements where the electromagnetic radiation produced by the electromagnetic radiation source is not directly detected by at least one photo detector.

Preferably, the light assembly comprises a plurality of electromagnetic radiation sources.

Further preferably, the light assembly comprises a plurality of electromagnetic radiation sources disposed in a matrix.

In use, the or each electromagnetic radiation source may comprise an LED.

Preferably, the at least one photo detector comprises a photodiode.

Further preferably, the light assembly comprises an optical waveguide coupled between the cover and the at least one photo detector.

In use, the optical waveguide may comprise a light pipe.

Preferably, the light pipe is configured as a solid transparent structure that contains the electromagnetic radiation by total internal reflection.

Further preferably, the light pipe is configured as a hollow structure having a generally circular cross-section that contains the electromagnetic radiation within a reflective lining.

In use, the light pipe may have a first end optically coupled to the cover, and an opposite second end which is optically coupled to the at least one photo detector.

Preferably, the light pipe is an extruded or moulded part of the cover.

In use, the cover may further comprise shielding means adjacent to the first end of the light pipe to prevent ambient electromagnetic radiation directly from entering the light pipe.

Preferably, the shielding means is an internally mirrored diaphragm.

Further preferably, the shielding means is a metalised foil or opaque window.

In use, the at least one photo detector may be disposed in the base.

Preferably, the electromagnetic radiation produced by the electromagnetic radiation source is visible light.

Further preferably, the electromagnetic radiation produced by the electromagnetic radiation source is selected from the group of X-rays, ultraviolet, infrared and microwaves.

In use, the at least one photo detector may detect the scattered light S' which is distributed through the cover, the scattered light S' being the sum of the forward light produced by the at least one electromagnetic radiation source F and the ambient light falling on the cover A.

Preferably, the scattered light from ambient light S'A is measured during a first period when the at least one electromagnetic radiation source is turned off.

Further preferably, the light assembly comprises a processing means for controlling the at least one electromagnetic radiation source and the at least one photo detector.

In use, an estimation of the scattered light from the forward light (S'F) may be obtained from the equation, S'(F+A)−S'A, where the scattered light from ambient light S'A is measured during a first period when the at least one electromagnetic radiation source is turned off.

Preferably, the processing means synchronises the measurement of the scattered light as the at least one electromagnetic radiation source is pulse width modulated on and off.

Further preferably, the output of the at least one photo detector is connected to a current-to-voltage converter implemented on an operational amplifier, the output of which is inputted to the processing means.

In use, the light assembly may further comprise two photo detectors connected in anti-phase to each other.

Preferably, the light assembly may further comprise a band pass filter coupled between the optical waveguide and the at least one photo detector, the band pass filter having a central wavelength that is matched to the wavelength of the at least one electromagnetic radiation source.

Also according to the present invention there is provided a method of measuring the electromagnetic radiation distributed within the cover of a light assembly of the first aspect of the invention, the method comprising the steps of:

turning on the at least one electromagnetic radiation source and measuring the electromagnetic radiation which is distributed through the cover using at least one photo detector optically isolated from the at least one electromagnetic radiation source;

turning off the at least one electromagnetic radiation source and measuring the radiation falling on the at least one photo detector; and subtracting the measured ambient electromagnetic radiation from the measured electromagnetic radiation to give an estimation of the total electromagnetic radiation flux emitted from the at least one electromagnetic radiation source.

Preferably, the method further comprising the step of.

matching the wavelength of the at least one electromagnetic radiation source to the at least one photo detector using a band pass filter.

Further preferably, the method further comprising the step of:

turning on the at least one electromagnetic radiation source and measuring the forward light which is distributed through the cover using two photo detectors connected in anti-phase.

In use, the steps of turning on the at least one electromagnetic radiation source and measuring the forward light which is distributed through the cover and turning off the at least one electromagnetic radiation source and measuring the ambient light falling on the at least one photo detector may be achieved by pulse width modulating the at least one electromagnetic radiation source on and off under the control of the processing means.

Further according to the present invention there is provided a computer program product for measuring the electromagnetic radiation distributed within the cover of a light assembly of the first aspect of the invention, comprising:

computer program product means for turning on the at least one electromagnetic radiation source and measuring the forward electromagnetic radiation which is distributed through the cover using at least one photo detector optically isolated from the at least one electromagnetic radiation source;

computer program product means for turning off the at least one electromagnetic radiation source and measuring the ambient electromagnetic radiation falling on the at least one photo detector; and computer program product means for subtracting the measured ambient electromagnetic radiation from the measured forward electromagnetic radiation to give an estimation of the total electromagnetic radiation flux emitted from the at least one electromagnetic radiation source.

It is believed that a light assembly that includes an integrated test facility at least addresses the problems outlined above. The advantages of the present invention are that an operator of the light assembly is able to diagnose the optical properties of the light source incorporated into the light assembly continuously during light assembly operation and in real time. The present invention also provides information on the protective cover surrounding the light assembly such as whether it is dirty, damaged or otherwise advising that the cover needs cleaning.

It will be obvious to those skilled in the art that variations of the present invention are possible and it is intended that the present invention may be used other than as specifically described herein.

BRIEF DESCRIPTION OF THE DRAWINGS

Specific non-limiting embodiments of the invention will now be described by way of example only and with reference to the accompanying drawings, in which.

DETAILED DESCRIPTION

Figure 1:
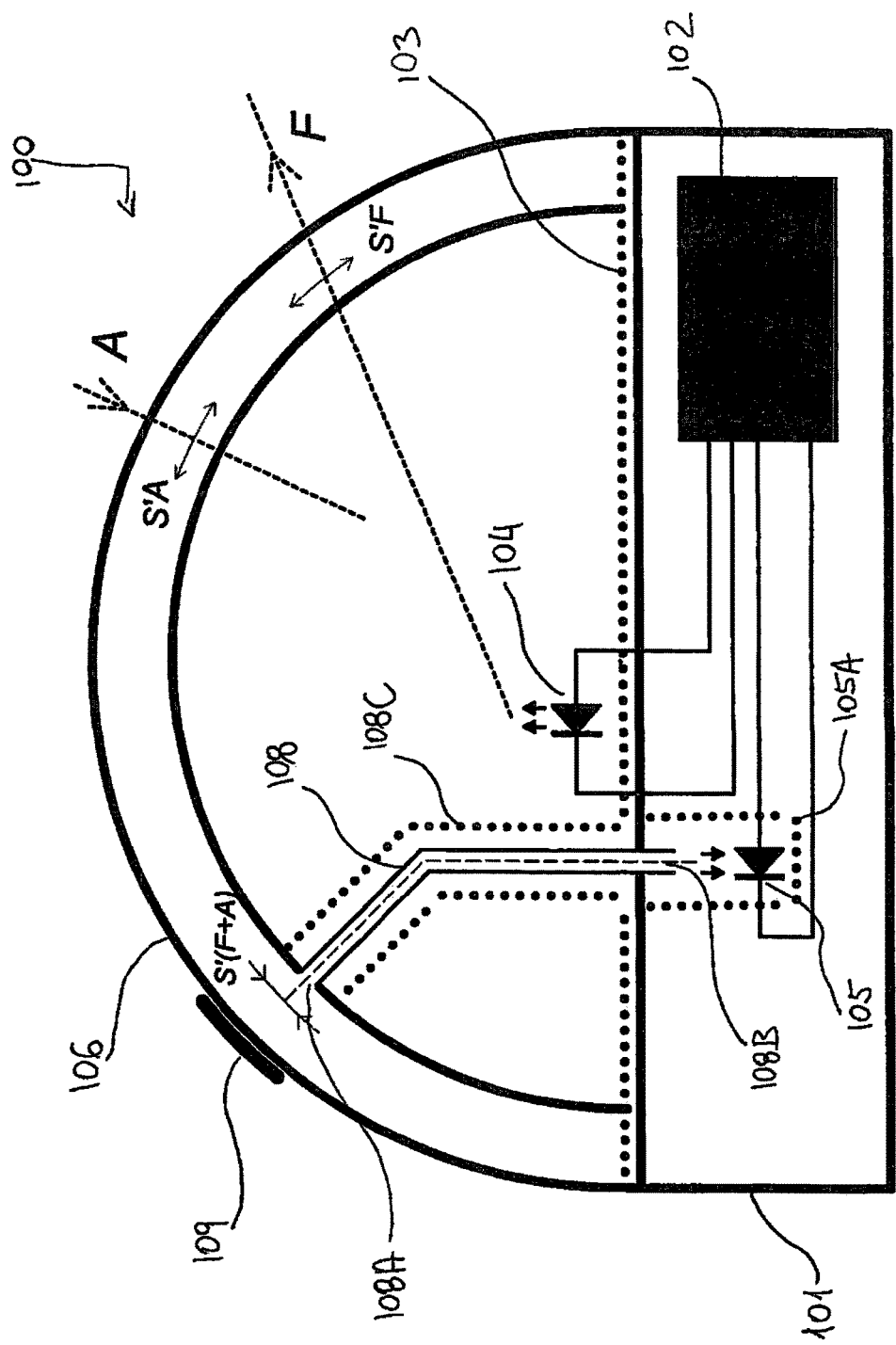
FIG. 1 is a cross sectional view of a first embodiment of a light assembly according to the present invention.

Referring now to the drawings, the light assembly 100 comprises a light source mounting base 101 having a generally planar non-transparent upper surface 103 and a hemispherical transparent plastics domed light cover 106 mounted sealingly to the surface 103 (e.g. by means of adhesive). A light source 104 is mounted on the upper surface 103 of the base 101 and, when actuated, projects light into and through the domed light cover 106. This light flux, which is transmitted through the domed light cover 106, is shown for illustration purposes only by light ray F in FIG. 1. In the embodiment shown in FIG. 1, the light source 104 is a semiconductor light emitting diode.

FIG. 1 also shows that an optical waveguide 108 extends between the domed light cover 106 and the interior of the base 101. The optical waveguide 108 is used for transporting the scattered light that is distributed throughout the hemispherical cover 106 to a photo detector 105 embedded in the light assembly 100. The photo detector 105 embedded in the light assembly 100 is optically shielded from stray light by optical shield 105A.

FIG. 1 shows that the photo detector 105 and the light source 104 are connected to a processing means 102 situated in the light assembly 100. The photo detector 105 is understood to be a device able to convert light flux to electrical quantities.

The optical waveguide 108 comprises a first portion 108A which extends perpendicularly from the inner surface of the hemispherical cover 106 and a second portion 108B, optically continuous with the first portion 108A, which passes perpendicularly through the planar upper surface 103 of the base 101. The walls of the optical waveguide 108, between the cover 106 and upper surface 103 of the case are coated by non-transparent light means 108C, which prevents any stray light from entering the optical waveguide 108 from the side walls 108C.

FIG. 1 also shows that, at the position where the first portion 108A of the optical waveguide 108 extends perpendicularly from the inner surface of the hemispherical transparent light cover 106, the outer surface of the light cover 106 is covered by an internally mirrored diaphragm 109 which prevents ambient or stray light from entering the optical waveguide 108 directly. The annular periphery of the domed lens 106, which abuts the surface of the base 101, is also internally mirrored for reflecting the scattered light distributed through the front protection lens 106.

It is important to note that the photo detector 105 is optically isolated from the light source 104 and never directly senses the light flux F from the light source 104 and/or the ambient light flux A that which is also distributed through the light cover 106. The ambient light flux, which is distributed through the light cover 106, is shown for illustration purposes only by line A in FIG. 1.

The photo detector 105 detects the scattered light S'(F+A) which is distributed through the hemispherical transparent light cover 106. An estimation of the scattered forward light S'F is a computation result S'(F+A)−S'A, where the scattered ambient light S'A is measured during a period when the light source 104 is turned off.

The skilled person will appreciate that if the ambient light A is reduced to zero by, for example, covering the light cover 106, then the output of the photo detector 105 is equal to the scattered forward light S'F only, and gives an estimation of the total light flux of the light source 104. By recording this value over successive measurements the present invention permits the quantification and recognition of degradation of the light source 104 before the risk of a critical failure.

Equally, by measuring the output of the photo detector 105 when the light source 104 is turned off, which can be achieved by synchronising the measurement to the pulse width modulated control signal, an estimation of the scattered ambient light S'A can be obtained. The measured scattered ambient light S'A therefore provides information on the domed light cover 106.

The photo detector 105 is therefore capable of measuring and diagnosing the light flux in the following conditions:
 i) total light flux in a wide range of offset light (ambient/background light);
 ii) light flux degradation due to aging or fault of the light source 104 within the light assembly 100;
 iii) hemispherical light cover 106 degradation due to accumulation of ice, dust and water vapour;
 iv) hemispherical light cover 106 degradation due to mechanical damage; and
 v) degradation of the light beam geometry due to mechanical damage.

Figure 2:
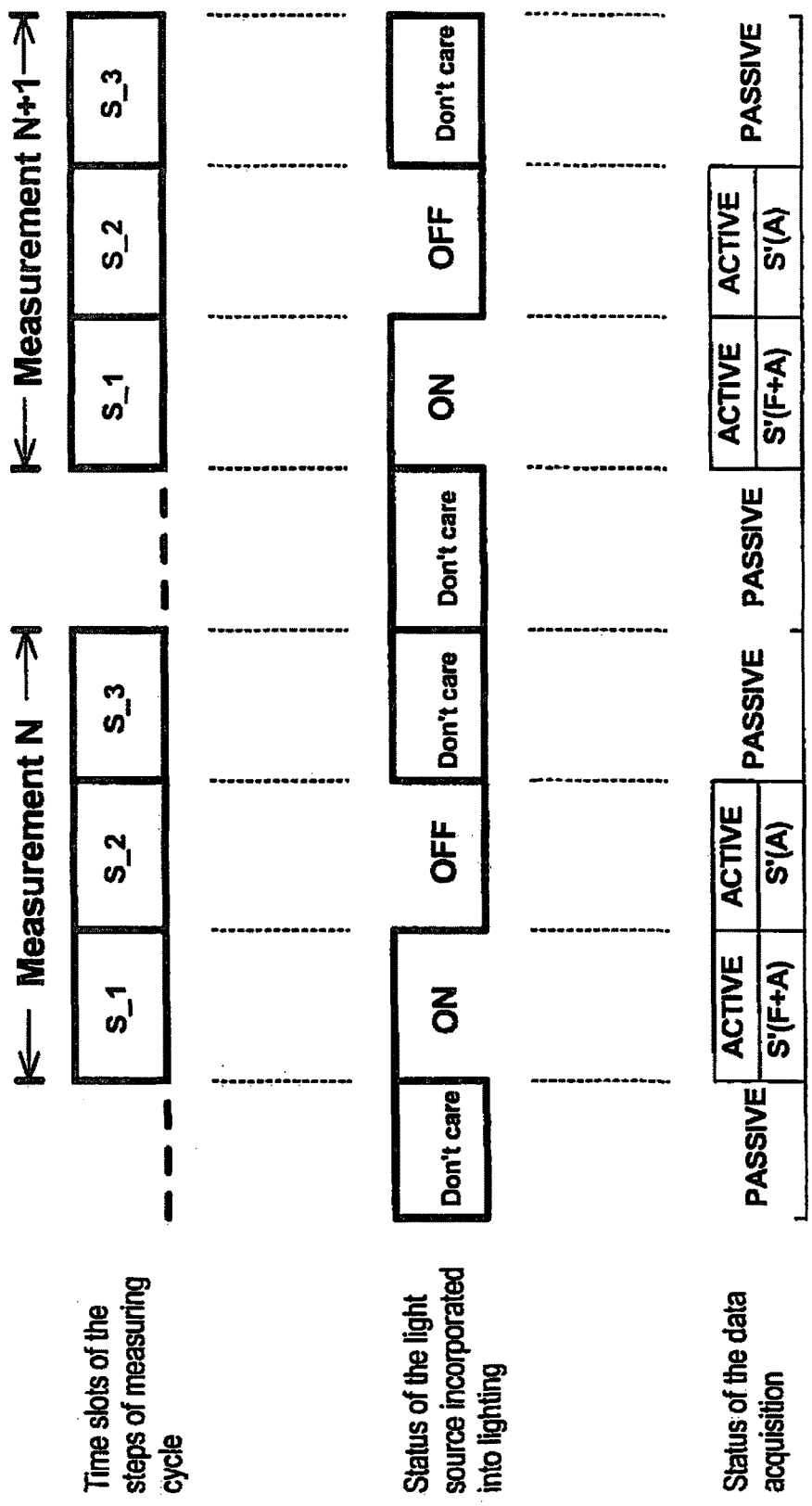
FIG. 2 shows a method of measuring the light flux distributed through the light cover of a light assembly according to the present invention.

FIG. 2 shows the method of measuring the light flux distributed through the light cover 106 of the light assembly 100 by measuring the output of the photo detector 105 when the light source 104 is turned on and off, which can be achieved by synchronising the measurement to pulse width modulated control signals.

As shown in FIG. 2, each measurement N essentially comprises three steps, numbered as steps S_1, S_2 and S_3. The first step S_1 of the measurement procedure involves turning on the light source 104 incorporated into light assembly 100 and measuring the scattered light from the total light flux distributed through the light cover 106 and recording the result as S'(F+A). The second step S_2 involves turning off the light source 104, previously energised in S_1, and measuring the scattered light from the total light flux distributed through the cover 106 and recording as a result S'A. The final and final step S_3 is to estimate the scattered light flux from the light source 104 energised in S_1 by subtracting the S'F=S'(F+A)−S'A.

Figure 3:
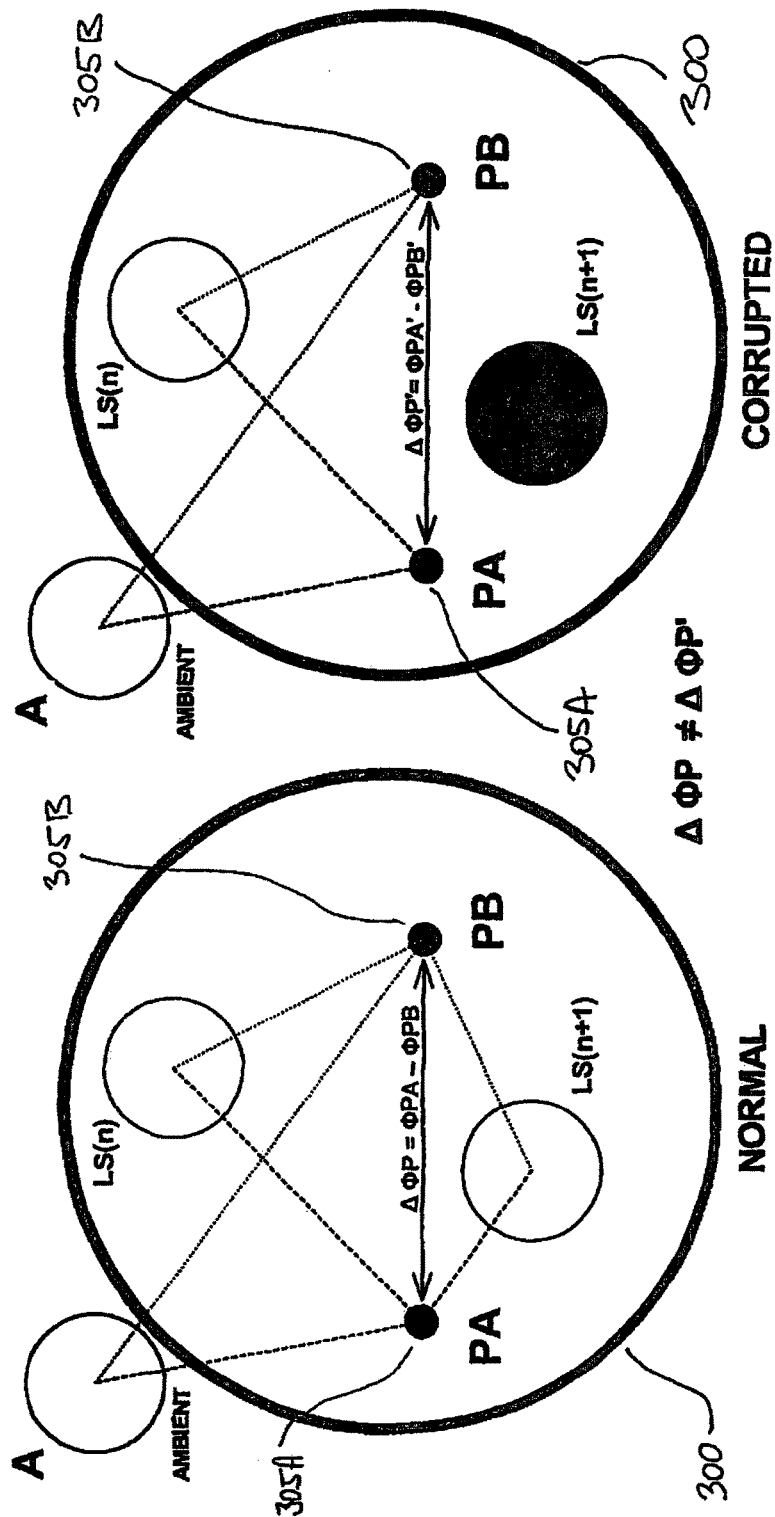
FIG. 3 is a plan view from above of a second embodiment of the light assembly according to the invention, where a differential measurement of the light fluxes is made at points PA and PB.

Whilst the embodiment shown in FIG. 1 shows how the present invention operates with a single photo detector 105 to measure the total ambient light and measure total light flux, in a further embodiment of the invention, as illustrated in FIG. 3, two or more photo detectors 305A and 305B located at points PA and PB, respectively, are able to perform a differential mode light measurement, as follows.

FIG. 3 shows schematically the principle of differential light measurement. The light assembly 300 of FIG. 3 is identical to that of the first embodiment, but a plurality of light sources LS are mounted on its planar upper surface. The light assembly of FIG. 3 is also provided with a hemispherical light cover 106, as in FIG. 1, which is not illustrated in FIG. 3. However, two optical waveguides (not shown), identical to the optical waveguide 108 of FIG. 1, are provided, each conveying light to a respective one of two photo detectors 305A and 305B located at points PA and PB, identical to the photo detector 105 of FIG. 1.

Measurements obtained using two differentially-connected photo detectors 305A and 305B respectively at points PA and PB gives better noise to signal ratio of processed signals because it measures the offset between light flux, at points PA and PB, which operate at the similar common mode signal level, as described above in relation to the embodiment of FIG. 1.

FIG. 3 shows that faulty light sources, respectively LS(n) and LS(n+1), incorporated into the light assembly 300 and/or damage to the light assembly 300 geometry and/or damage to the light output aperture of respectively LS(n) and LS(n+1) will cause changes in the distributed light flux $\Phi(PA\_A)$, $\Phi(PA\_LSn)$, $\Phi(PA\_LSn+1)$ and/or $\Phi(PB\_A)$, $\Phi(PBL\_Sn)$, $\Phi(PB\_LSn+1)$, respectively, and will change the light flux offset respectively $\Delta\Phi P$, $\Delta\Phi P'$ between points PA and PB, which will be outputted as an imbalanced signal. The light flux offset respectively $\Delta\Phi P$, $\Delta\Phi P'$ between points PA and PB are therefore constant in uniform ambient light A as long as the magnitudes of distributed light flux from the light sources respectively LS(n) and LS(n+1) incorporated into the light assembly 300 stay unchanged and/or properties of light distribution path within the light assembly 300 stay unchanged.

In use, the differentially-connected photo detectors light flux measurement is particularly useful in an application where light sources LS incorporated into the light assembly 300 are connected in a matrix, such as LEDs to produce a high intensity output light flux and/or output light flux of specific geometry.

In the left hand figure of FIG. 3, the total brightness of the two differentially-connected photo detectors 305A and 305B located at points PA or PB and each receiving light from a respective optical waveguide, is a sum of the brightness contributed by the plurality of light sources LS and the ambient light measurement A.

The brightness offset between points PA and PB is therefore constant in uniform ambient light A as long as the distributed light fluxes from the light sources LS and the assembly geometry stays unchanged, and the output from the differentially-connected photo detectors 305A and 305B is therefore equal and opposite.

A faulty light source (in the example shown in the right hand of FIG. 3, light source LS(n+1) 6 starts to degrade) or damage to the assembly geometry will cause changes in the distributed light fluxes, and will change the brightness offset between points PA and PB which will be outputted from the differentially-connected photo detectors positioned at points PA or PB as an imbalance signal.

The differential mode of operation is particularly useful in LED aviation applications where the high intensity output of the light assembly 300 makes it difficult to recognise and detect degradation from a common mode measurement. For example, a high power LED landing light might contain 19 LEDs disposed in matrix producing a peak intensity 400,000 cd. A measurement obtained using the "common mode" technique described in relation to FIG. 1 would give us information about the total light flux and front cover 106. Measurements obtained using two differentially-connected photo detectors 305A and 305B gives better resolution because it measures the brightness offset between points PA and PB which helps to more accurately detect light flux degradation due to aging or failure of the LEDs disposed within the light assembly 300.

Figure 4:
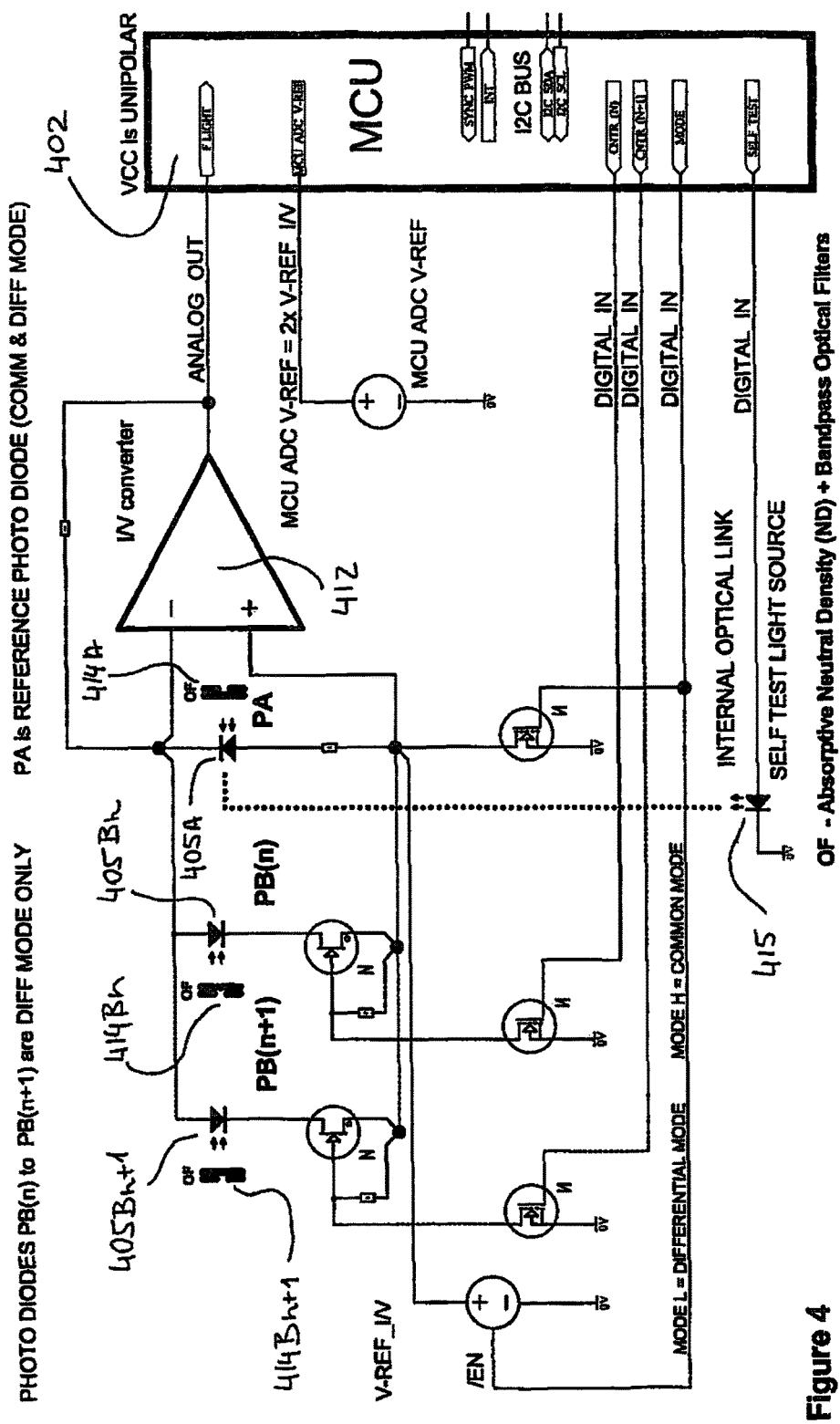
FIG. 4 is a schematic diagram showing how the present invention can be implemented under the control of a microprocessor.

FIG. 4 is a schematic diagram showing how the common mode and differential measurement techniques of the present invention can be implemented using a microprocessor-controlled electronic detection circuit.

FIG. 4 shows a schematic diagram of an electronic circuit which is to monitor a number photo detectors 405A, 405Bn, 405Bn+1. This detection circuit is realised using a processing means 402 such as a microprocessor. The skilled person will appreciate that, in operation, a set of instructions or algorithm written in software in the processing means continually monitors the output of a current-to-voltage converter implemented on an operational amplifier 412 which has a number photo detectors 405A, 405Bn, 405Bn+1 connected at its input. The skilled person will also appreciate that for purposes of clarity many of the analogue signals being inputted to the processing means 402 are first converted to digital form by any suitable type of analogue-to-digital (ADC) conversion. This ADC conversion is not shown in FIG. 4. Other circuit functions such as, for example, bus interfaces and memory are also not expressly shown in FIG. 4.

FIG. 4 shows that in a common mode of operation, photo detectors 405Bn and 405Bn+1 are disabled and the output of a single photo detector 405A positioned at point PA in the light assembly is processed by the current-to-voltage converter implemented on the operational amplifier 412. In common mode operation, the output of the current-to-voltage converter is proportional to the scattered light S'(F+A) which is distributed through the hemispherical cover 106.

In the differential mode of operation, the photo detector 405A at point PA is used as a reference signal source to differentially connect one-at-a-time, photo detectors respectively 405Bn, 405Bn+1 positioned in the detector matrix. In differential mode of operation, the imbalance in scattered light between the reference point PA and a given measurement point PB or PBn+1 will force an imbalanced signal on the output of current-to-voltage converter.

FIG. 4 also shows that the present invention can include a self-test built-in light source 415 optically connected to the photo detector 405A, which can be used to validate the photo detector 405A response to the optical stimulus.

The estimation of scattered light from the light source forward light (S'F) is a computation result S'(F+A)−S'A, where the scattered light S'A from ambient is measured during the period when the light sources are off. This can be achieved by synchronising the measurements as the light sources are pulse width modulated on and off under the control of the processing means 50.

By implementing the present invention in software, the photo detector's 405A, 405Bn, 405Bn+1 optical parameters, including QE and dark current, are subject to temperature shift and can be compensated for by software. It is also possible, in software, to compensate for the light source temperature to give better measurement discrimination.

FIG. 4 also shows that optical input aperture of the photo detectors respectively 405A, 405Bn, 405Bn+1 are each covered by absorptive neutral density and band pass optical filters OF.

Various alterations and modifications may be made to the present invention without departing from the scope of the invention. For example, although particular embodiments refer to a light assembly with sources of light understood to be a source of electromagnetic radiation whose significant part of the power radiated spectrum is infrared IR and/or visible spectrum VIS and/or ultraviolet UV, this can include, but not limited to, light emitting semiconductor devices and/or filament bulbs and/or incandescent bulbs.

The invention claimed is:

1. A light assembly, comprising:
   a base;
   at least one electromagnetic radiation source mounted on the base;
   a cover located over the base, the cover being transparent to the electromagnetic radiation produced by the at least one electromagnetic radiation source; and
   at least one photo detector, optically isolated from the at least one electromagnetic radiation source, the at least one photo detector being configured to receive electromagnetic radiation conveyed by the cover.

2. The light assembly as claimed in claim 1, further comprising a plurality of electromagnetic radiation sources.

3. The light assembly as claimed in claim 1, further comprising a plurality of electromagnetic radiation sources disposed in a matrix.

4. The light assembly as claimed in claim 1, wherein each electromagnetic radiation source comprises an LED.

5. The light assembly as claimed in claim 1, wherein the at least one photo detector comprises a photodiode.

6. The light assembly as claimed in claim 1, further comprising an optical waveguide coupled between the cover and the at least one photo detector.

7. The light assembly as claimed in claim 6, wherein the optical waveguide comprises a light pipe.

8. The light assembly as claimed in claim 7, wherein the light pipe is configured as a solid transparent structure that contains the electromagnetic radiation by total internal reflection.

9. The light assembly as claimed in claim 7, wherein the light pipe is configured as a hollow structure having a generally circular cross-section that contains the electromagnetic radiation within a reflective lining.

10. The light assembly as claimed in claim 7, wherein the light pipe has a first end optically coupled to the cover, and an opposite second end which is optically coupled to the at least one photo detector.

11. The light assembly as claimed in claim 10, wherein the cover further comprises shielding means adjacent to the first end of the light pipe to prevent ambient electromagnetic radiation directly from entering the light pipe.

12. The light assembly as claimed in claim 11, wherein the shielding means is an internally mirrored diaphragm.

13. The light assembly as claimed in claim 11, wherein the shielding means is a metalised foil or opaque window.

14. The light assembly as claimed in claim 7, wherein the light pipe is an extruded or moulded part of the cover.

15. The light assembly as claimed in claim 6, further comprising a band pass filter coupled between the optical waveguide and the at least one photo detector, the band pass filter having a central wavelength that is matched to a wavelength of the at least one electromagnetic radiation source.

16. The light assembly as claimed in claim 1, wherein the at least one photo detector is disposed in the base.

17. The light assembly as claimed in claim 1, wherein the electromagnetic radiation produced by the at least one electromagnetic radiation source is visible light.

18. The light assembly as claimed in claim 1, wherein the electromagnetic radiation produced by the at least one electromagnetic radiation source is selected from the group consisting of X-rays, ultraviolet, infrared and microwaves.

19. The light assembly as claimed in claim 1, wherein the at least one photo detector detects scattered light S' which is distributed through the cover, the scattered light S' being the sum of the forward light produced by the at least one electromagnetic radiation source F and the ambient light falling on the cover A.

20. The light assembly as claimed in claim 19, wherein the scattered light from ambient light S'A is measured during a first period when the at least one electromagnetic radiation source is turned off.

21. The light assembly as claimed in claim 1, further comprising a processing means for controlling the at least one electromagnetic radiation source and the at least one photo detector.

22. The light assembly as claimed in claim 21, wherein an estimation of the scattered light from the forward light (S'F) is obtained from the equation, S'(F+A)−S'A, where the scattered light from ambient light S'A is measured during a first period when the at least one electromagnetic radiation source is turned off.

23. The light assembly as claimed in claim 21, wherein the processing means synchronizes the measurement of the scattered light as the at least one electromagnetic radiation source is pulse width modulated on and off.

24. The light assembly as claimed in claim 1, wherein the output of the at least one photo detector is connected to a current-to-voltage converter implemented on an operational amplifier, the output of which is inputted to the processing means.

25. The light assembly as claimed in claim 1, further comprising two photo detectors connected in anti-phase to each other.

26. A method of measuring electromagnetic radiation distributed within a cover of a light assembly, the method comprising:
    turning on at least one electromagnetic radiation source and measuring the electromagnetic radiation which is distributed through the cover using at least one photo detector optically isolated from the at least one electromagnetic radiation source;
    turning off the at least one electromagnetic radiation source and measuring electromagnetic radiation falling on the at least one photo detector; and
    subtracting measured ambient electromagnetic radiation from the measured electromagnetic radiation to provide an estimation of total electromagnetic radiation flux emitted from the at least one electromagnetic radiation source.

27. The method as claimed in claim 26, further comprising:
    matching a wavelength of the at least one electromagnetic radiation source to the at least one photo detector using a band pass filter.

28. The method as claimed in claim 26, further comprising:
    turning on the at least one electromagnetic radiation source and measuring forward light which is distributed through the cover using two photo detectors connected in anti-phase.

29. The method as claimed in claim 26, wherein turning on the at least one electromagnetic radiation source and measuring the forward light which is distributed through the cover and turning off the at least one electromagnetic radiation source and measuring the ambient light falling on the at least one photo detector is achieved by pulse width modulating the at least one electromagnetic radiation source on and off under control of processing means for controlling the at least one electromagnetic radiation source and the at least one photo detector.

30. A non-transitory computer readable-medium embodied therein instructions being executable by at least one processor to perform a method for measuring electromagnetic radiation distributed within a cover of a light assembly, the method comprising:
    turning on at least one electromagnetic radiation source and measuring forward electromagnetic radiation which is distributed through the cover using at least one photo detector optically isolated from the at least one electromagnetic radiation source;
    turning off the at least one electromagnetic radiation source and measuring ambient electromagnetic radiation falling on the at least one photo detector; and
    subtracting the measured ambient electromagnetic radiation from the measured forward electromagnetic radiation to provide an estimation of total electromagnetic radiation flux emitted from the at least one electromagnetic radiation source.

31. A light assembly, comprising:
    a base;
    at least one electromagnetic radiation source mounted on the base;
    a cover located over the base, the cover being transparent to the electromagnetic radiation produced by the at least one electromagnetic radiation source and through which light passes out of the light assembly; and
    at least one photo detector, optically isolated from the at least one electromagnetic radiation source, the at least one photo detector being configured to receive electromagnetic radiation conveyed by the cover.

* * * * *